US00RE40166E

(19) United States
(12) Reissued Patent
Sukhorukov et al.

(10) Patent Number: US RE40,166 E
(45) Date of Reissued Patent: Mar. 25, 2008

(54) MAGNETIC NON-DESTRUCTIVE METHOD AND APPARATUS FOR MEASUREMENT OF CROSS SECTIONAL AREA AND DETECTION OF LOCAL FLAWS IN ELONGATED FERROUS OBJECTS IN RESPONSE TO LONGITUDINALLY SPACED SENSORS IN AN INTER-POLE AREA

(75) Inventors: Vasily Vasilievich Sukhorukov, Moscow (RU); Serguei Borisovich Belitsky, Moscow (RU)

(73) Assignee: Intron Plus, Ltd., Moscow (RU)

(21) Appl. No.: 10/640,107

(22) Filed: Aug. 13, 2003

Related U.S. Patent Documents

Reissue of:
(64) Patent No.: 6,492,808
Issued: Dec. 10, 2002
Appl. No.: 09/606,747
Filed: Jun. 29, 2000

(30) Foreign Application Priority Data

Dec. 17, 1999 (RU) ..... N99126933/28

(51) Int. Cl.
*G01N 27/82* (2006.01)

(52) U.S. Cl. ..... 324/242; 324/235; 324/240
(58) Field of Classification Search ..... 324/235, 324/237, 238, 260–262, 225–230, 240–243
See application file for complete search history.

(56) References Cited

U.S. PATENT DOCUMENTS 4,659,991 A * 4/1987 Weischedel ..... 324/241
5,565,771 A * 10/1996 Hamelin et al. ..... 324/225
5,804,964 A * 9/1998 Hamelin et al. ..... 324/242

* cited by examiner

*Primary Examiner*—Bot LeDynh
(74) *Attorney, Agent, or Firm*—Harter Secrest & Emery LLP; Brian Shaw, Esq.; Stephen B. Sabi, Esq.

(57) ABSTRACT

A magnetic non-destructive method and an apparatus for measurement of cross sectional area of elongated ferrous objects such as steel wire ropes and for detecting local flaws is disclosed. A section of a wire rope is magnetized by longitudinally spaced magnetic poles. A magnetic field parameter, e.g. magnetic flux density, is measured in, by at least, one pair of points between the poles of magnetizing device (in an inter-pole area) at the object under test surface. The pair of points is formed by two sensors placed in the inter-pole area along a direct line parallel to the rope axis. The rope cross sectional area corresponds to a sum of the sensor pair signals. Local flaws, such as broken wires and pitting corrosion in the rope, is detected by a first differences of signals of the sensor pair. At least one additional magneto-sensitive sensor is located radially inward of the poles and weight coefficient A depending on a nominal value of the rope cross sectional area is subtracted from the sum of signals of the sensor pair thereby providing a second difference of the signals corresponding to the rope cross sectional area. The coefficient A value is chosen to get the minimum value of the second signal difference while the magnetizing device and all the sensors are placed onto the rope having a nominal value of a cross sectional area. A sensor unit in the inter-pole area includes a magnetic core in form of three longitudinally spaced ferrous elements. Pairs of the sensors are located in the gaps along a direct line parallel to the rope. Two embodiments of the magnetic heads are disclosed: the hollow cylinder-shaped one and the U-shaped one.

27 Claims, 3 Drawing Sheets

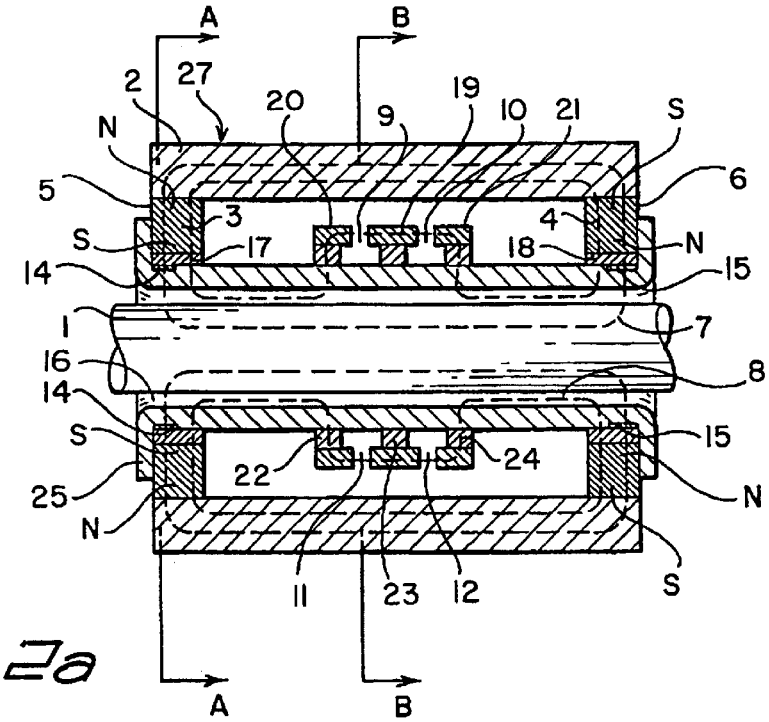
FIG. 2a
FIG. 2b
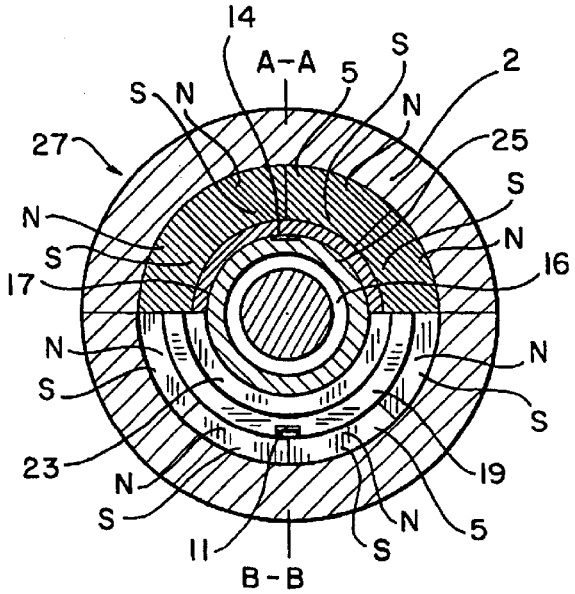

MAGNETIC NON-DESTRUCTIVE METHOD AND APPARATUS FOR MEASUREMENT OF CROSS SECTIONAL AREA AND DETECTION OF LOCAL FLAWS IN ELONGATED FERROUS OBJECTS IN RESPONSE TO LONGITUDINALLY SPACED SENSORS IN AN INTER-POLE AREA

Matter enclosed in heavy brackets [ ] appears in the original patent but forms no part of this reissue specification; matter printed in italics indicates the additions made by reissue.

The present application claims priority benefits under 35 U.S.C. §119 to Russian Federation application N99126933/28 filed Dec. 17, 1999.

1. Field of the Invention

The present invention relates to the non-destructive testing of product quality, and in particular, to magnetic testing of elongated ferromagnetic objects like steel rods, tubes and wires to determine variances in a cross sectional area of object as well as the presence of local flaws.

2. Background of the Invention

A method and apparatus for magnetic non-destructive testing of elongated objects, e.g. steel ropes, by measurement of loss of metallic area (LMA) due to wearing and for local flaw (LF) detecting are described in U.S. Pat. No. 4,659,991, US C1. 324/241, Int.C1.G01N27/82, issuing in 1987. The method includes the axial magnetizing of the rope part by permanent magnets to a condition close to magnetic saturation and measuring the magnetic flux leakage variation near the rope surface by using sensing coils, in which an electromotive force (emf) is induced while rope moves relative to the magnets.

The disadvantage of the method of U.S. Pat. No. 4,659,991 is the insufficient accuracy of the LMA measurement as the method requires the measurement of a very small leakage flux change, resulting from a small value of the LMA (about one percent), at the significant initial level of the flux passing through the coils by the nominal rope cross sectional area.

The magnetic flux leakage change caused by LMA is quite commensurate with the flux leakage variation due to the magnetic flux instability of the magnet, particularly, when the environment temperature and hence, temperature of the permanent magnets, is changed. In addition, the emf in the coils is induced only while a rope moves relative to the coils and the emf depends on the rate of travel of the rope. Thus, the apparatus of U.S. Pat. No. 4,659,991 is relatively complicated and requires decreasing the speed and influence on measure readings. In addition, measurement is not possible when the rope is not traveling.

Also known in the prior art is a steel wire rope flaw detector in which there is no rope speed influence on readings (see, e.g. U.S. Pat. No. 5,565,771, Int.C1. G01N 27/72, 1996). The flaw detector disclosed in the '771 patent contains magnetizing means with poles encircling a rope under test and Hall sensors. The sensors are located in gaps between poles of the magnetizing means and the rope. The second portion of the sensors are positioned in a gap of a magnetic core which is formed by a ferrous ring encircling the rope and by a ring-shaped magnetic shield with three-leg shape of cross section. The magnetic shield shields the second portion of the Hall sensors from magnetic field of the poles. The second Hall sensor portion provides LF detecting by magnetic flux leakage induced by the LF. A digital signal processor processes signals of all the Hall sensors.

The flaw detector of U.S. Pat. No. 5,565,771 is more convenient due to Hall sensor signals being independent of rope speed and their measure is possible when the rope is stopped. However, the flaw detector sensitivity to LF increases due to the ferrous magnetic core use.

The LMA measurement accuracy is often insufficient because of slight dependence of the magnetic flux density in the gaps between the poles of the magnetizing means and the rope from area of the rope cross section. The reason is that magnetic flux via the gaps is defined by the magnetizing means and by use of the high-energy modem permanent magnets. Magnetic flux density changes in the gaps around the rope, when the rope cross section changes only due to redistribution of magnetic flux portions: the main flux through the rope and the flux leakage in magnetizing means inter pole space. Relative change of the main flux is significantly less than the flux leakage relative change. That is why the relative change of Hall sensor voltage is insignificant. This results in an error caused by small voltage change of Hall sensor at high initial level of the voltage, and particularly, the temperature error is significant.

Further, LF detecting reliability of the flaw detector of U.S. Pat. No. 5,565,771 is often not sufficient. This appears to be due to the location of the Hall sensors in the magnetic core gap between the ring encircling the rope and the ring shield of three-leg shaped cross section. When the LF gets to the zone of sensitivity of the sensor, the leakage flux, induced by the LF and captured by the magnetic core, is divided into two portions. One portion goes through the gap with the Hall sensors and the remaining portion goes trough the three-leg shaped magnetic core bypassing the Hall sensors. Consequently, the LF signal of the Hall sensor decreases because of the bypass effect as like as LF detecting reliability. Accordingly, the accuracy of rope under test cross sectional area measurement is insufficient as well as the reliability of LF detecting.

Therefore the need exists for an apparatus for the magnetic testing of elongated ferromagnetic objects like steel rods, tubes, wires, wherein increased accuracy is achieved.

SUMMARY OF THE INVENTION

An object of the present invention is the solution of the problem of increasing the accuracy of cross sectional area measurements and local flaw detection in steel wire ropes. A further object of the invention is increasing the reliability of LF detecting in elongate ferrous objects.

In accordance with the method of the present invention, a section of an object under test, e.g. of a steel wire rope, is magnetized longitudinally by a magnetizing device having poles spaced along a longitudinal dimension of the wire rope. The longitudinal spacing of the poles along the longitudinal dimension of the rope defines a longitudinally extending inter-pole area between the poles. A magnetic field parameter, e.g. magnetic flux density, is measured by magneto-sensitive sensors forming a pair, in at least one pair of points in an area between the spaced poles (the inter-pole area) at the object surface. The pair of sensors is formed by two sensors placed along a line, which is parallel to the longitudinal axis of the rope in area of the most homogeneous magnetic field in the inter-pole space.

The rope cross sectional area is defined by a sum of the signals from the sensor pair. When the rope cross sectional area is changed, the magnetic fluxes through the rope and through the area surrounding the rope are redistributed. In particular, loss of the rope cross section metallic area (LMA) leads to an increase in magnetic flux leakage within the inter-pole space round the rope, which increases magnetic flux density in the inter-pole area. The relative increase of the leakage flux occurs significantly more than the relative decrease in the base flux. Therefore, a resulting signal change from the sensors within the inter-pole space is significantly more than the signal change of the sensors in the gaps between the poles and the rope. This provides an increased LMA measurement accuracy.

A further increase in accuracy is provided by a subtraction of additional magneto-sensitive sensor signals from the sum of the sensor pair signals. The additional sensor signal is provided from a sensor located in a gap between the rope under test and a pole of the magnetizing device. That is, along a radius extending from the longitudinal axis of the rope, there is the rope surface, the additional sensor and then the pole of the magnetizing device. The resulting second signal difference is used to measure LMA. Thus, an LMA measurement error, from the instability of magnetic flux density round the rope, e.g. from the influence of temperature variation on the magnetizing device, is decreased.

The presence of a LF in the rope is detected by a first signal difference of sensors forming the pairs. When a rope section under test contains no LF, then signals from the sensors in a pair equal each other and the first difference of the signals is close to zero. If the section, containing a LF, gets to a sensitivity zone of one of the sensors in the pair, then magnetic field homogeneity is destroyed in the zone due to a local magnetic flux leakage induced by the LF. The pair of the first sensors is thus unbalanced and the first signal difference differs from zero. Unavoidable radial displacements of the rope during a test do not destroy magnetic field homogeneity. Due to this, the output signal of the sensor pair remains close to zero, thus a noise level, e.g. because of rope vibration, is low. An increased signal to noise ratio is thereby provided as well as LF detecting reliability.

The flaw detector includes a magnetizing device, having poles spaced along the longitudinal axis of the rope and inducing a sufficient magnetic flux to provide magnetic saturation of the section of a rope being tested, a sensor unit located between the poles, a digital signal processor and a recorder. The sensor includes magneto-sensitive sensors and a magnetic core. The magnetic core is arranged as three ferrous elements surrounding the rope and positioned with respect to each other along the rope with gaps in which pairs of the magneto-sensitive sensors are located. Each the pairs is formed by two sensors located in gaps between the ferrous elements of the core on a direct line, which is parallel to the longitudinal axis of the rope.

BRIEF DESCRIPTION OF THE DRAWINGS

The following figures show preferred embodiments of the invention, which are illustrated in the following detailed description.

FIG. 2a is a cross sectional view of the magnetic head with the magnetizing device and the sensor unit having a cylindrical form.

FIG. 2b is a cross sectional view with a top half taken along lines A—A of FIG. 2a and a bottom half taken along lines B—B of FIG. 2a.

FIG. 3b is a cross sectional view with a top half taken along lines A—A of FIG. 3a and a bottom half taken along lines B—B of FIG. 3a.

DETAILED DESCRIPTION OF THE PREFERRED EMBODIMENTS

The present description is set forth in terms of the magnetic non-destructive measurement of a cross-sectional area of an elongated ferrous object such as a steel rod, tube, wire or wire rope. It is understood the cross section of these structures can define a circular, curvilinear, rectangular, triangular, or faceted profile. For purposes of description the term "rope" or "wire rope" shall be understood to encompass each of these structures. Since NDT of steel ropes in use is an actual problem, this particular case is set forth in an exemplary manner below.

Figure 1A:
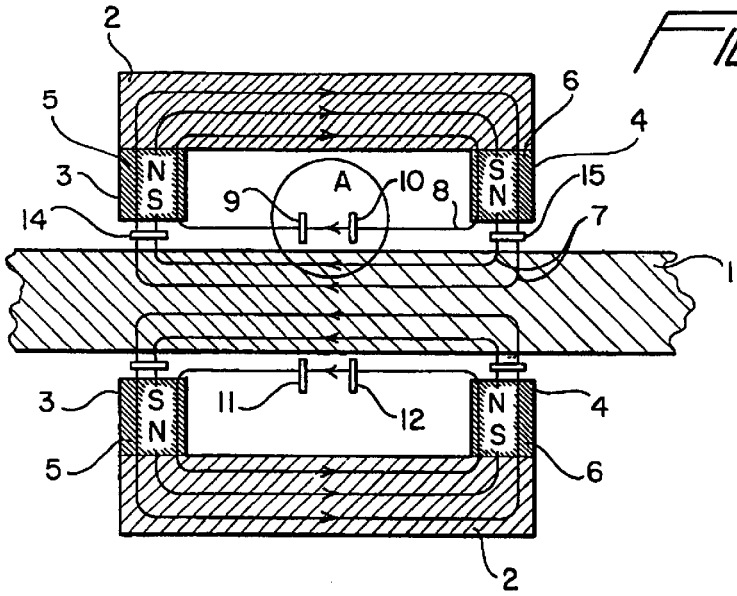
FIG. 1a is a cross sectional view of the magnetizing device providing a magnetic flux in the rope under test, the magneto-sensitive sensors and the magnetic flux distribution, wherein a section of rope under test contains no LF.
Figure 3A:
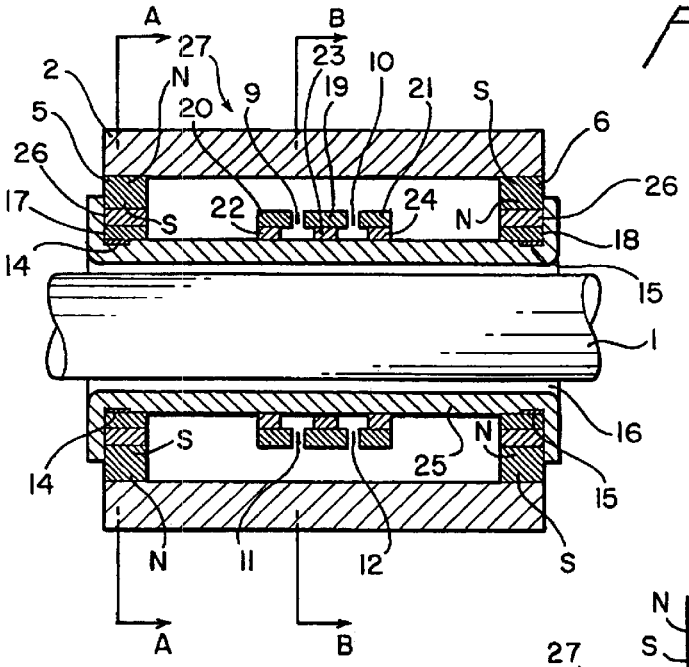
FIG. 3a cross sectional view of an alternative the flaw detector magnetic head with a U-shaped magnetic core of the magnetizing device laced on the rope under test.
Figure 3B:
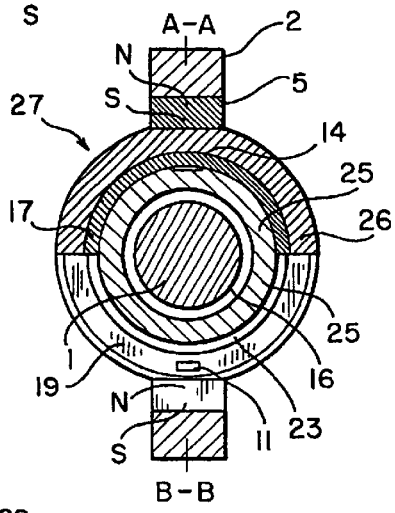

Referring to FIG. 1, the magnetic flux through a rope 1 under test is provided by a magnetizing device 40 having a magnetic core 2 with spaced apart poles 3, 4 on the ends adjacent to and facing the rope 1. The poles 3, 4 are spaced along the longitudinal axis of the rope 1. The spaced apart poles 3, 4 thereby define an inter-pole area (or length) extending parallel to the longitudinal axis between the longitudinally spaced poles. The poles 3, 4 are formed by permanent magnets 5 and 6 as shown in FIG. 1. However, it is understood the poles 3, 4 can be formed by pole-pieces surrounding the rope 1 under test. The magnetic core 2 is made of soft-iron material. The magnetizing device 40 is hollow cylindrical shape, surrounding the rope under test 1, as shown in FIG. 2. Alternatively, the core 2 may include one, two (as shown in FIG. 3) or more U-shaped parts.

A direct or alternating current can be used in the magnetizing device 40 to create the magnetic flux through the rope 1 under test.

The main part of the full magnetic flux induced by the magnetizing device 40 extends through the rope 1 under test and forms a base flux 7. A leakage flux 8 as a part of the full flux extends through air in the inter-pole area, i.e. between the poles 3 and 4. The leakage flux 8 is most homogeneous in the center of the inter-pole area.

Magneto-sensitive sensors 9 and 10 are located adjacent to the rope 1 surface on a direct line parallel to the longitudinal axis of the rope 1 and are symmetrically located relative to a center plane of inter-pole area between the poles 3, 4. That is, the sensors 9, 10 are symmetrically disposed about a centerline of the two longitudinally spaced poles 3, 4. The magneto-sensitive sensors 9, 10 form a pair of sensors.

It is preferable to use Hall generators as the magneto-sensitive sensors 9, 10. The sensors 9, 10 measure the magnetic flux density in this configuration.

In addition, it is preferable to measure the magnetic flux density of the leakage flux 8 by the pair of similar sensors 11, 12 located diametrically across the rope 1 from the sensors 9, 10.

Signals of the sensors 9, 10 (11, 12) correspond to a LMA value of the rope 1 under test and the presence of a LF in the section.

A change in the cross sectional area of the rope 1 leads to magnetic flux redistribution in the rope 1 and the area surrounding the rope 1. Particularly, the LMA leads to a leakage flux increase in the inter-pole area, consequently, increasing the magnetic flux density in the inter-pole area. The relative increase of the leakage flux 8 is significantly more than the relative decrease of the base flux 7 because of the leakage flux 8 is significantly less then the base flux 7. Hence, a relative change of magnetic flux density in the inter-pole area surrounding the rope 1 is significantly more than in gaps between the poles 3, 4 and the rope 1 under test.

Due to this relative change in fluxes, the LMA measurement accuracy is higher as compared to prior devices, where the LMA is measured using signal change of sensors located in gaps between the poles 3, 4 of the magnetizing device and the rope 1, i. e. using the base flux change.

The metallic area (MA) value is defined by a sum of the sensor 9–12 pair signals referencing the sum value to a nominal value of MA. Additional increase in the measurement accuracy of the MA is attained by the summation, because of increase of the LMA measure channel sensitivity without a gain change of the channel. Consequently, measurement errors from gain instability of the channel do not change and the signal to noise ratio increases. Increase of the accuracy of the measurement is thus obtained.

Figure 1B:
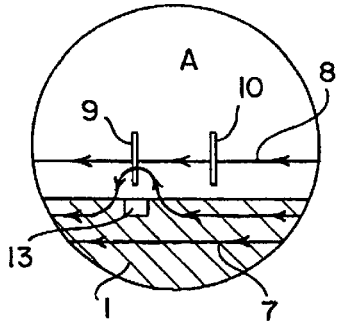
FIG. 1b is a cross sectional view of the magnetizing device providing a magnetic flux in the rope under test, the magneto-sensitive sensors and the magnetic flux distribution, wherein a section of rope under test contains a LF.

Local flaws (LF) of the rope 1, e.g. a gap 13 between the ends of a wire broken shown in FIG. 1b, are detected by using a difference of signals of the sensor pairs 9, 10 and 11, 12, e.g. by using the difference of signals of sensors 9 and 10, or 11 and 12. This difference is defined as a first signal difference.

The sensor unit can be supplied by several pairs of sensors like the pairs 9, 10 and 11, 12, which are placed on a circumference about the rope 1 under test in the inter-pole area.

Therefore, use of the first signal difference of sensors 9, 10 (11, 12) provides an increase in the signal to noise ratio, when subject to vibration or other disturbance influences. Consequently, the LF detecting reliability is increased.

Additional magneto-sensitive sensors 14 (15) can be placed in the radial gap between the pole 3 (4) of the magnetizing device 40 and the adjacent portion of the rope 1 as shown in FIGS. 1a, 2a, 2b, 3a and 3b. Subtraction of a sensor 14 (15) signal, modified by a weight coefficient A, from the sum of signals of the sensor pairs 9, 10 and 11, 12, provides a second signal difference which is used to measure the MA (or the LMA) of the rope 1. The weight coefficient A is a constant obtained by testing ropes with identical nominal MA values. The coefficient value is chosen to provide a minimum value of the second signal difference when the rope under test MA equals a nominal value, i.e. the LMA equals to zero.

This provides additional increase in measurement accuracy due to decrease of measurement error caused by instability of the flux density round the rope 1, e.g. due to temperature variation influence on the magnetizing device 40. When the temperature of the magnetization device 40 changes, the base magnetic flux 7 provided by the device also changes. This leads to a change of the leakage flux 8 and its density on which the Hall sensors, and the signals from sensors 9, 10 and 11, 12 are correspondingly changed. Simultaneously, the base magnetic flux 7 and its density under the poles 3, 4 of the magnetizing device 40 change to the same side. Therefore, the second signal difference changes only by a negligible amount when the base magnetic flux 7 of the magnetizing device 40 changes. Thus, the MA measurement accuracy of the rope 1 increases.

To set the weight coefficient A, a magnetic head is placed on a rope 1 part with a nominal value of MA and then the coefficient A is varied so to get a minimal magnitude of the second signal difference. Due to this, higher accuracy is reached. In this case, the second signal difference of sensor signals is directly proportional to the MA change relative to a nominal value. It is necessary to measure small changes of MA (of the order of one percent of nominal value) by non-destructive testing of steel ropes. Measurement of slight changes of the sensor signals relative to a level close to zero allows obtaining a higher accuracy than the same measurement relative to a significant original level.

Thus, the method according to the invention provides higher accuracy by measurement of the MA and higher reliability of the LF detecting in steel ropes.

The apparatus includes the magnetizing device 40 (FIG. 2) in which permanent magnets 5, 6 with the poles 3, 4 are facing a channel 16 for receiving the rope 1 under test. The poles 3, 4 of the magnetizing device 40 can be supplied by accessory inserts 17, 18 made of soft-iron material and are snug against inner side of the poles 3, 4.

The sensor unit magnetic core consists of the elements 19, 20, 21 and is placed between the poles 3, 4 of the magnetizing device 40. The middle element 19 of the sensor unit magnetic core is located along the longitudinal axis of the rope 1 in the middle of the inter-pole area. Two identical side elements 20 and 21 are located along the channel 16 axis to form symmetric gaps relative to the middle element 19. All the elements 19–21 are formed as rings made of soft-iron material. The middle element 19 can be displaced slightly relative to the middle of inter-pole area, but a central placement is believed to provide the best testing accuracy.

The ferrous inserts 22, 23, 24 are snugged in a coaxial relation against inner side of the elements 19, 20, 21 respectively.

The magneto-sensitive sensors 9, 10, forming a pair of sensors of the sensor unit, are placed in the gaps between the middle element 19 and the side elements 20, 21 of the sensor unit magnetic core. Another pair of magneto-sensitive sensors 11, 12 of the sensor unit is located symmetrically on the opposite side of the channel 16. Several such pairs of sensors can be uniformly placed in gaps about a circumference in the channel 16.

One or several additional magneto-sensitive sensors 14, 15 can be placed under the poles 3, 4 of the magnetizing device 40.

Various types of sensors (magneto-resistors, magneto-transistors, magneto-diodes etc.) can be used as the magneto-sensitive sensors at the sensor unit. However, it has been found most advantageous to employ Hall effect generators because of their high sensitivity to magnetic flux density variation and stability.

A shell 25 made of non-ferrous material is placed under the poles 3, 4 along the entire magnetizing device 40. The shell 25 forms the smooth channel 16, through which the rope 1 passes. The shell 25 reduces damage of the sensors 9–12 of the sensor unit and the additional sensors 14, 15 from passage of the rope 1. The shell 25 also limits possible radial vibration and skewing of the rope 1 within the channel 16. The accessory nonferrous shell 25 is advantageously made of a nonferrous metal or alloy, i.e. brass to be wear resistant. A preferred material of the shell 25 for ropes having a damageable protective coating, e.g. a polymer, is a plastic, e.g. polyvinyl chloride (PVC) since a metallic shell could damage the protective coating.

The ferrous inserts 17, 18, 22, 23, 24 and the nonferrous shall 25 are formed as replaceable accessories and are of several standard sizes, since the apparatus is intended for testing of ropes having various diameter within predetermined range.

Another embodiment of the apparatus according to the invention disclosed in FIG. 3 is employed primarily for testing of ropes located close each to other, e.g. elevator ropes. In these situations, the distance between adjoining elevator ropes is typically about 80 mm. The embodiment of FIG. 2 is not convenient for elevator ropes testing because of space limitation for the magnetization device 40 and the sensor unit location.

The embodiment of FIG. 3 is analogous to the embodiment disclosed in FIG. 2 as can be seen by comparison of their longitudinal cross sections. A difference is that the magnetic core 2 of the magnetization device in the embodiment FIG. 3 has a U-shape profile and the permanent magnets 5, 6 are provided by the pole pieces 26. The pole pieces 26 encircle the channel 16 and the ferrous inserts 17, 18 to form a continuous loop. Since the external diameter of the pole pieces 26 is significantly less than the height of the magnetic core 2 of the magnetization device 40, the apparatus clearance along a traverse or cross sectional axis is significantly less than in a perpendicular axis. Due to the constriction of the apparatus along one axis, the apparatus can be located around the rope 1 under test even by small distance between ropes.

For more convenient use of the embodiments FIG. 2 and FIG. 3, the magnetic systems which are symmetrical relative to the axis of the channel 16, the magnetizing device and the sensor unit are constructed as split halves along a longitudinal plane of symmetry. The halves can be joined on one side of the channel 16 axis by hinges (not shown in the drawings) and retained by a lock (not shown).

Figure 4:
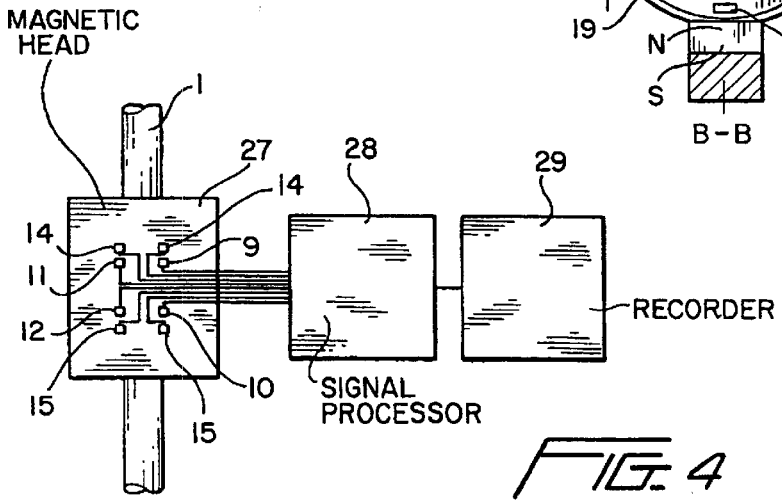
FIG. 4 is a block-diagram of the flaw detector.

The magnetization device and the sensor unit are assembled together (FIG. 4) forming the magnetic head 27 for location adjacent the rope 1 under test.

Located in the magnetic head 27 are sensors 9–12 of the sensor unit and the additional sensors 14, 15 under the poles 3, 4 of the magnetization device. The sensors are connected to a signal-processing unit 28, e.g. to a digital signal processor. An output of the signal-processing unit 28 is connected to a recorder 29, e.g. to a printer which prints a chart diagram, a display screen or a data storage device.

It is also understood, the magnetic head 27 can be provided in any embodiment by a track generator for definition of a distance from a rope 1 zero point to a current point on a record. As track generators are well known, the track generator is not shown on the drawings.

The flaw detector operates in the following manner.

The magnetic head 27 is placed on the rope 1 under test and generates a longitudinal magnetic flux 7 in the rope by the magnetizing device 40 containing magnets 5, 6 and the magnet core 2. Magnets 5, 6 magnetize a section under test of the rope 1 to substantially magnetic saturation.

The base part 7 of the magnetic flux induced by the magnetizing device 40 passes through the rope 1 and the leakage flux 8 passes through the inter-pole area surrounding the rope 1 intermediate of the poles. The inter-pole leakage flux 8 (or its portion) intersects the ferrous elements 19–21 of the sensor unit magnet core and the pairs of the Hall sensors 9, 10 and 11, 12.

The sensor 9, 10 and 11, 12 signals in form of the Hall electromotive force (emf.) are supplied to the digital processor 28 where they processed according to the present method. Results, or output from the signal processor 28 are recorded by the recorder 29, e.g. by a printer, in form of traces figured by the track generator in length units, e.g. in meters. One trace displays the LMA of the rope 1 value in percent of the nominal value of a cross section and another trace displays the LF signals.

The inter-pole flux leakage 8 intersecting the elements 19, 20 and 21 depends on the rope 1 cross sectional area. Thus, the signal sum of sensors the 9–12, forming the pairs (as well as of others similar pairs of sensors surrounding the rope 1), corresponds to the rope 1 cross sectional area. The signal processor 28 adds the signal of sensors 9, 10 as well as the signal of sensors 11, 12 and any other similar sensor pairs. The printer 29 creates a chart record of the rope LMA from the signal sum of the sensors and of signal of the track generator by the processor 28.

Since the leakage flux 8 is significantly less than the base flux 7, then the relative increase (in case of the LMA) of the leakage flux 8 is significantly more than the relative decrease of the base flux resulting from redistribution of the fluxes due to a change in the rope 1 cross sectional area. Consequently, the relative change of magnetic flow density in the inter-pole area surrounding the rope 1 is significantly greater than the corresponding change in the gaps between the poles 3, 4 and the rope 1. The use of the larger relative change provides an increased accuracy in measurements.

Signals of the additional sensors 14 and 15 placed under the poles 3, 4 of the magnetization device 40 as modified by the weight coefficient A are deducted from the sum of signals of the pairs 9–10, 11–12 and any other sensor pairs, after averaging by the signal processor 28. By deducting the signal of the additional sensors 14, 15 as multiplied by the weight coefficient A, from the sum of signals, the second signal difference is obtained which is used to measure the cross section of the rope 1. Thus, the measurement accuracy increases since the measurement error associated with instability of magnetic flux density from temperature variations and other random factors decreases.

The first signal difference of the sensors 9 and 10 as well as 11 and 12, and of any other similar sensor pairs is close to zero if a rope section, located within zone of sensitivity of the sensors, has no LF, such as broken wires. The same flux leakage 8 passes through the sensors 9 and 10 in this case. The same applies to the sensors 11 and 12 as well as to any other sensor pairs. Consequently, a sum of the first differences of the sensor pairs signals is close to zero when there are no wires broken of the rope 1 within the zone of sensitivity of the sensors 9–10, 11–12.

Figure 5:
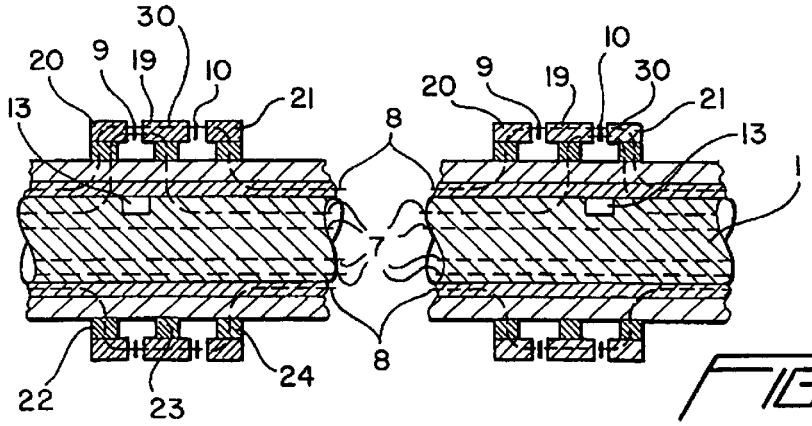
FIG. 5 is a cross sectional view showing the influence of a broken wire rope on the magnetic flux distribution through the rope under test and through the magneto-sensitive sensors.

When a wire broken end 13 of the rope 1 gets into the zone of sensitivity of the sensors, e.g. into the zone of sensitivity of the sensor 9, a local flux leakage 30 arises which is caught by the elements 19 and 20 of sensor unit magnetic core (see FIG. 5). As a result, the total flux leakage, passing through the sensor 9, increases and the first difference of signals of the sensor pair 9 and 10 increases.

When the wire broken end 13 moves into the zone of sensitivity of the sensor 10, the total flux leakage through this sensor increases and the first difference of signals of the sensor pair 9–10 changes in sign. This creates a bipolar pulse of the Hall emf at the output of the sensor pair 9–10. The pulse is recorded by the recorder 29 after processing by the signal processor 28 and can be identified as the signal of rope 1 wire broken.

Thus, signals of the sensors 9–12 correspond to a cross sectional area of an object under test and upon the presence of the LF in the section. The sum of the signals corresponding to the cross sectional area of the rope in the sensor sensitivity zone and the first signal difference of sensors of each pair corresponds to the presence of the LF in the rope in the sensor sensitivity zone.

Since the same sensors are used in the apparatus to measure the LMA of a section of the rope 1 and to detect the LF in the section, then signals of the LMA channel and of the LF channel appear simultaneously when a section of the rope 1 with the LF gets into sensitivity zone of sensors 9–12. Additional increase of the LF detecting reliability is provided by comparison of signals of both channels. A further benefit results from a simplification of the design is simplified because quantity of magneto-sensitive sensors decreases.

When a rope 1 of a smaller cross section is to be tested, the radial gaps between the elements 19–21 of the sensor unit, the magnetic core and the rope increase. This leads to spread of the ring zones of sensor sensitivity and to their mutual overlap. This appears as the first signal difference of sensor pairs 9, 10 (11, 12) decreases and a decrease in the LF detection reliability of the rope 1. In addition, an increase of the gaps decreases sensitivity of the sensors 9–12 to the LF of the rope 1, which in turn leads to additional decrease of the LF detection reliability. The accessory ferrous inserts 22–24 inside the elements 19–21 decreases the radial gaps between the rope 1 and the elements 19–21 of the sensor unit magnetic core, thereby providing for the highest reliability of the LF detection by various nominal value of the object 1 under test cross sectional area.

An increase of radial gaps also takes place under the poles 3, 4 of the magnetizing device 40 when the rope 1 under test cross sectional nominal value decreases. This leads to decrease of magnetic flux density in the rope 1 as well as the rope material going from a magnetically saturated (or substantially saturated) condition to non-saturated condition. Consequently, the linear dependence of magnetic flux density to the cross sectional area of the rope 1 is destroyed in a zone of measuring it by the sensors 14 (15). This leads to an increase of error in the cross sectional area measurement. Location of the accessory ferrous inserts 17, 18 under the poles 3, 4 provides the radial gaps between the poles 3, 4 and the rope 1 are sufficiently small to maintain the rope 1 material in a condition close to, or at magnetic saturation. Thus, the measurement error does not increase by testing a rope having less than the nominal cross sectional area.

Additional increase of measurement accuracy of the rope 1 cross sectional area is provided by the middle element 19 location in the middle of the inter-pole area, as the magnetic system of the magnetization device 40 and of the sensor unit becomes symmetrical. If the magnetic system is not symmetrical, then an additional error appears because of magnetic hysteresis phenomena in the rope by travel of the rope 1 relative to the magnetization device.

The flaw detector is calibrated by the following way prior to the LF measurements. The calibration procedure of the flaw detector is divided into two stages: at a first stage the channel of the LMA measure is calibrated, and at a second stage the LF channel is calibrated.

At the first stage, the magnetic head 27 is placed on a section of the rope 1 having a nominal value of cross sectional area that correlates to the zero value of the rope LMA. Using the signal processor 28, one fixes the coefficient A value to obtain a zero value of LMA at the recorder 29. Then, the magnetic head 27 is placed on a section of the rope 1 having a known value of LMA and one gets this value on the recorder 29 using the signal processor 28. Two points of a calibration coefficient are thus obtained.

Calibration by the two points provides sufficient measurement accuracy as the sensor signal dependence on the LMA value is close to a linear dependency. When the relationship is non-linear, significantly more than two points calibration points are used. That is, two or more sections of a rope with different known LMA values are used for calibration.

It is possible to use 100% value of the LMA, which correlates to absence of the rope 1 within the magnetic head 27. This is the end of the first stage calibration procedure.

At the second stage of the calibration procedure, the magnetic head 27 is placed on the rope section having broken wires of known cross sectional area, e.g. 1% of nominal value of the rope 1 of a nominal cross sectional area. Moving the magnetic head 27 along the rope 1 section, a pulse of a wire broken signal is generated and ultimately recorded on a chart record of the recorder 29 after adjustment to a proper magnitude by the signal processor 28. This is the end of the calibration procedure.

Industrial Application

The present invention can be used in all areas of technology for producing and using elongated ferromagnetic objects like steel rods, tubes, wires and ropes (as round so flat ones) for non-destructive testing of objects mentioned and, first of all, for checking of steel wire rope wear by measuring their cross sectional area and by detecting local flaws like broken wires and local corrosion in them. It can be used, in particular, for checking ropes in mining, at rope ways, at elevators, at cranes, at rope bridges.

While the invention has been described with reference to preferred embodiments, it will be understood by those skilled in the art that various changes may be made and equivalents may be substituted for elements thereof without departing from the scope of the invention. In addition, many modifications may be made to adapt a particular situation of material to the teachings of the invention without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A method of monitoring a cross sectional area of an elongated ferrous object having a longitudinal axis, the method comprising:

(a) magnetizing longitudinal section of the object between two magnetic poles spaced apart along the longitudinal axis to magnetically saturate a section of the object;

(b) measuring a magnetic field parameter *with first and second sensors located* at [a first and a second] longitudinally spaced apart [location] *locations* intermediate the two magnetic poles; *and*

(c) determining one of a change in a cross sectional area of the object and presence of a local flaw in the object corresponding to the measured parameter.

2. The method of claim 1, wherein determining the presence of a local flaw includes subtracting a first sensor signal from a second sensor signal.

3. The method of claim 1, wherein determining the change in cross sectional area includes adding a first sensor signal to a second sensor signal.

4. The method of claim 1, further comprising measuring the magnetic field parameter at symmetric locations relative to the spaced apart poles along the longitudinal axis.

5. The method of claim 1, further comprising measuring a magnetic field parameter at an additional sensor located intermediate one pole and an adjacent section of the object, adjusting a signal from the additional sensor by a known coefficient to provide a resultant and subtracting the resultant from a summation of a first sensor and a second sensor signal.

6. An apparatus for monitoring a cross sectional area of an elongated ferrous object having a longitudinal axis, comprising:

(a) a pair of magnetic poles spaced along the longitudinal axis to define an inter-pole area;

(b) a first pair of longitudinally spaced apart magnetic sensors in the inter-pole area; and (c) a processor connected to the magnetic sensors to provide a signal corresponding to one of a MA or LF in the elongated ferrous object.

7. The apparatus of claim 6, further comprising an additional magnetic sensor radial inward of a magnetic pole at the same longitudinal location as the magnetic pole.

8. The apparatus of claim 6, further comprising a second pair of longitudinally spaced magnetic sensors in the inter-pole area.

9. The apparatus of claim 8, wherein the first pair of sensors are diametrically opposed to the second pair of magnetic sensors.

10. The apparatus of claim 6, wherein the processor is selected to add the signals from the magnetic sensors to determine the MA.

11. The apparatus of claim 6, wherein the processor is selected to subtract the signals from the magnetic sensors to determine the LF.

12. The apparatus of claim 6, wherein the magnetic sensors are Hall effect sensors.

13. A method for the magnetic non-destructive detection of a local flaw an elongated ferrous object having a longitudinal axis, the method comprising:

(a) longitudinally magnetizing a section of the object section by a magnetizing device having longitudinally spaced apart poles directed toward the object to substantially magnetically saturate the object section;

(b) measuring a magnetic field parameter within an inter-pole area longitudinally intermediate the spaced apart poles, in at least one pair of spaced points within the inter-pole area by a pair of magneto-sensitive sensors disposed along a line parallel to the longitudinal axis; and (c) deducting signals of the sensors forming the pair from other to provide a first signal difference corresponding to the presence of a local flaw in the object.

14. A method for the magnetic non-destructive measurement of a cross sectional area of an elongated ferrous object having a longitudinal axis, the method comprising:

(a) longitudinally magnetizing a section of the object section by a magnetizing device having poles longitudinally spaced apart poles directed toward the object to substantially magnetically saturate the object section;

(b) measuring a magnetic field parameter within an inter-pole area at a surface of the object, in at least one pair of longitudinally spaced points within the inter-pole area by a pair of magneto-sensitive sensors disposed along a line parallel to the longitudinal axis; and (c) determining a cross sectional area dependent value corresponding to a sum of signals of the pair of magneto-sensitive sensors.

15. The method of claim 14, wherein the magnetic field parameter is measured at points symmetrical relative to a longitudinal canter of the spaced poles.

16. The method of claim 14, further comprising modifying the sum by subtracting an additional signal from a sensor radially intermediate one of the poles and object.

17. The method of claim 16, further comprising multiplying the additional signal by a weight coefficient.

18. The method of claim 16, further comprising corresponding the weight coefficient to a nominal value of the object.

19. The method of claim 17, further comprising selecting a value of the weight coefficient to provide a minimum value of a second difference of the sensor signals while the magnetizing device and the first sensor pair are disposed to test an object having a nominal value of cross sectional area.

20. Apparatus for a magnetic non-detective measurement of cross sectional area of elongated ferrous objects and for a detection of a local flaw, comprising:

(a) a pair of longitudinally spaced magnetic poles directed toward a channel through which the object passes, the poles sufficient to substantially magnetically saturate the object, the poles defining an inter-pole area; and (b) a sensor unit located in the inter-pole area, the sensor unit including a magnetic core and a pair of magneto-sensitive sensors, the magnetic core having three longitudinally spaced ferrous elements, wherein two of the spaced ferrous elements are symmetrically spaced about a remaining one of the spaced ferrous elements to form a pair of gaps, the pair of sensors longitudinally spaced and located in the pair of gaps, respectively along a line parallel to the longitudinal axis.

21. The apparatus of claim 20, further comprising a signal processor connected to the sensor unit.

22. The apparatus of claim 20, further comprising a non-ferrous shell located radially inside the magnetic poles and the sensor unit, the shell sized to form a channel through which the object passes.

23. The apparatus of claim 20, wherein the spaced ferrous elements include ferrous inserts located inside the ferrous elements.

24. The apparatus of claim 20, further comprising inserts disposed radially inward of the poles.

25. The apparatus of claim 20, further comprising at least one magneto-sensitive sensor disposed radially inward of one of the magnetic poles.

26. The apparatus of claim 20, wherein the magneto-sensitive sensors are Hall effect sensors.

27. The apparatus of claim 20, wherein the spaced ferrous elements and the pair of sensors are symmetrically located about a longitudinal center point of the inter-pole area.

* * * * *